United States Patent [19]

Barris et al.

[11] Patent Number: 5,024,054
[45] Date of Patent: Jun. 18, 1991

[54] ENGINE EXHAUST SYSTEM WITH SEQUENTIAL LOADING OF MULTIPLE FILTERS

[75] Inventors: Marty A. Barris, Lakeville; Wayne M. Wagner, Apple Valley, both of Minn.

[73] Assignee: Donaldson Company, Inc., Minneapolis, Minn.

[21] Appl. No.: 607,601

[22] Filed: Oct. 31, 1990

Related U.S. Application Data

[63] Continuation of Ser. No. 456,334, Dec. 26, 1989, abandoned.

[51] Int. Cl.$^5$ .............................................. G01N 3/02
[52] U.S. Cl. ........................................ 60/274; 60/286; 60/288; 60/311
[58] Field of Search .................. 60/274, 286, 288, 311

[56] References Cited

U.S. PATENT DOCUMENTS

| | | |
|---|---|---|
| 3,783,619 | 1/1974 | Alquist .................................. 60/288 |
| 4,276,071 | 6/1981 | Outland . |
| 4,281,512 | 8/1981 | Mills . |
| 4,373,330 | 2/1983 | Stark . |
| 4,427,418 | 1/1984 | Kogiso et al. . |
| 4,485,622 | 12/1984 | Takagi et al. . |
| 4,494,375 | 1/1985 | Rao et al. . |
| 4,506,505 | 3/1985 | Melzer . |
| 4,509,327 | 4/1985 | Enga . |
| 4,512,147 | 4/1985 | Wong ..................................... 60/274 |
| 4,516,993 | 5/1985 | Takeuchi et al. . |
| 4,573,317 | 3/1986 | Ludecke . |
| 4,597,262 | 7/1986 | Retallick . |
| 4,625,511 | 12/1986 | Scheitlin et al. . |
| 4,641,496 | 2/1987 | Wade . |
| 4,651,524 | 3/1987 | Brighton . |
| 4,663,934 | 5/1987 | Sickels . |
| 4,671,059 | 6/1987 | Lawson . |
| 4,685,291 | 8/1987 | Ha . |
| 4,709,547 | 12/1987 | Pischinger et al. . |
| 4,720,972 | 1/1988 | Rao et al. . |
| 4,791,785 | 12/1988 | Hudson et al. . |
| 4,851,015 | 7/1989 | Wagner ................................. 60/313 |
| 4,899,540 | 2/1990 | Wagner et al. . |

FOREIGN PATENT DOCUMENTS

2166191 8/1973 Fed. Rep. of Germany ........ 60/288

OTHER PUBLICATIONS

Donaldson Drawing No. 5215B94.

*Primary Examiner*—Douglas Hart
*Attorney, Agent, or Firm*—Merchant, Gould, Smith, Edell, Welter & Schmidt

[57] ABSTRACT

In a diesel engine exhaust system a plurality of valved ceramic filters are connected in parallel in the exhaust stream and loaded sequentially. While one filter is preferentially loaded, a second filter is opened to the exhaust stream when backpressure reaches a predetermined value. The secondary filter is removed from the exhaust stream when air flow to the engine drops a discrete amount below a peak air flow determined by the backpressure which would cause the secondary filter to be placed in the exhaust stream. The preferentially loaded filter is bypassed when completely loaded and regenerated. The secondary filter is then preferentially loaded and the sequence continues.

9 Claims, 6 Drawing Sheets

ENGINE EXHAUST SYSTEM WITH SEQUENTIAL LOADING OF MULTIPLE FILTERS

This is a continuation divisional of application Ser. No. 07/456,334, filed Dec. 26, 1989, and now abandoned.

FIELD OF THE INVENTION

This invention relates to diesel engine exhaust treatment systems, and, in particular, to means for deciding how to load multiple filters and when to regenerate loaded filters and thereafter to best utilize the other filters.

BACKGROUND OF THE INVENTION

It is known in the art to provide a diesel engine with an exhaust treatment system that includes one or more particulate traps or filters that are operative to filter out and collect particulates from the exhaust gas stream discharged from the engine. Such particulates consist largely of carbon particles that tend to plug the filter, thus restricting exhaust gas flow therethrough. Accordingly, after continued use of such a system for a period of time dependent on engine operation, it becomes desirable to effect regeneration of the filter.

Diesel engine exhaust traps are currently being manufactured by Corning and others. The trap is of a ceramic material and is placed in line in series with the exhaust pipe so that all exhaust gases must go through the trap. The trap is constructed such that the gases must pass through a ceramic wall with very small pore size in order to escape to the atmosphere. As the pores become clogged, a backpressure arises upstream of the trap.

Due to manufacturing limitations in the size of ceramic filters, some engine applications require several filters so that the backpressure remains below engine specifications at all engine conditions. As one or more filters become loaded, regeneration must be effected and, consequently, filters being regenerated are bypassed from the exhaust stream and are unavailable for filtering. In some systems, three or more filters may be used. The means of deciding how to load multiple filters, when to regenerate them, and how to best utilize unloaded filters is not a trivial problem. The present invention is directed to a methodology for operation of such a system.

SUMMARY OF THE INVENTION

The present invention is directed to apparatus for reducing particulates from exhaust gases of an engine. The apparatus includes an exhaust line in fluid communication with the engine and a plurality of exhaust filtration assemblies connected in parallel with one another with each being in fluid communication with the exhaust line. Each of the assemblies includes a filter and a valve with the valve being between the engine and the filter. The apparatus also includes mechanism for regenerating the filters and mechanism for controlling the regenerating mechanism and the valves to preferentially load a first of the filters and use another of the filters to alleviate backpressure during high air flow conditions until the first filter is loaded and then to preferentially load a second of the filters while alleviating backpressure during high air flow conditions with yet a third of the filters and to continue sequentially loading the filters in this fashion. The controlling mechanism operates the valves to bypass the filters when loaded and operates the regenerating mechanism to regenerate the filters when loaded and bypassed.

The invention is also directed to a method for selecting among multiple filters for placement in an exhaust stream of an engine in order to load the filters with particulates and for removal from the stream in order to regenerate the filters. The method includes the steps of placing a first filter in the stream, sensing backpressure in the stream between the filter and the engine, placing a second filter in the stream when the backpressure is greater than a first predetermined value, sensing air flow to the engine, and removing the second filter from the stream when the air flow is less than a second predetermined value.

In another embodiment of the method, parameters for use in a predetermined method of determining when the first filter requires regeneration are sensed. When regeneration is required, the second filter is placed in the exhaust stream and the first filter is removed from the stream for regeneration.

More particularly, a system of three filters can have two available for filtering while a third is regenerating. Of the two filters, one is primary and the other is secondary. The present system is designed to preferentially load the primary filter as long as the engine backpressure is below its specified limits. As the primary filter loads with soot, exhaust flow resistance increases. At higher engine speeds, the backpressure reaches the engine limits sooner and sooner. When the backpressure limit is reached, the secondary filter is opened to the exhaust stream to split the flow and reduce the backpressure. At this point, the system changes from a single filter mode to a dual filter mode configuration. The dual mode configuration, as indicated, is based on engine flow and on the loading level of the primary filter. When the proper amount of loading of the primary filter has been reached, it is bypassed for regeneration, and the secondary filter becomes the primary. The previously regenerated filter (the third filter in the system) then becomes the new secondary. The system continues to sequentially use the filters.

Between the single and dual filter modes, there is a dividing line which represents peak flows allowable for a single filter (as dictated by backpressure) which is a function of the loading of the filter (see FIG. 7). The greater the primary filter loading, the lower the allowable flow before the dual filter mode is engaged. The present invention is further directed to creating a dead band region below the indicated dividing line at a level of approximately 75% of the flow function. That is, once the system is in the dual filter mode, the exhaust flow must fall below the dead band before the system reverts to the single filter mode. This prevents excessive switching between modes.

The invention thusly summarized will be better understood by reference to the drawings briefly described hereinafter and the detailed description provided thereafter.

DETAILED DESCRIPTION OF THE PREFERRED EMBODIMENT

Figure 1:
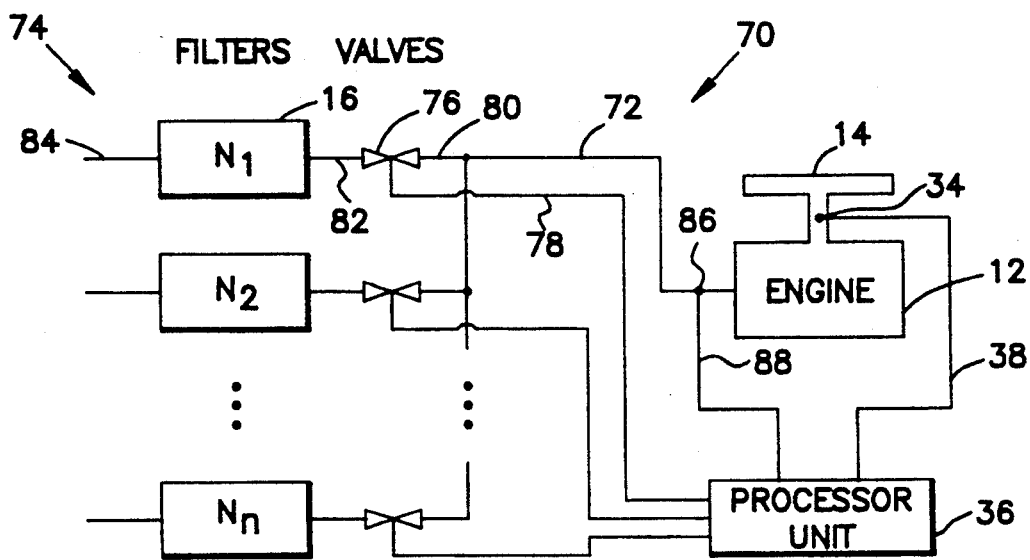
FIG. 1 is a schematic illustration of an engine exhaust treatment system in accordance with the present invention.
Figure 4:
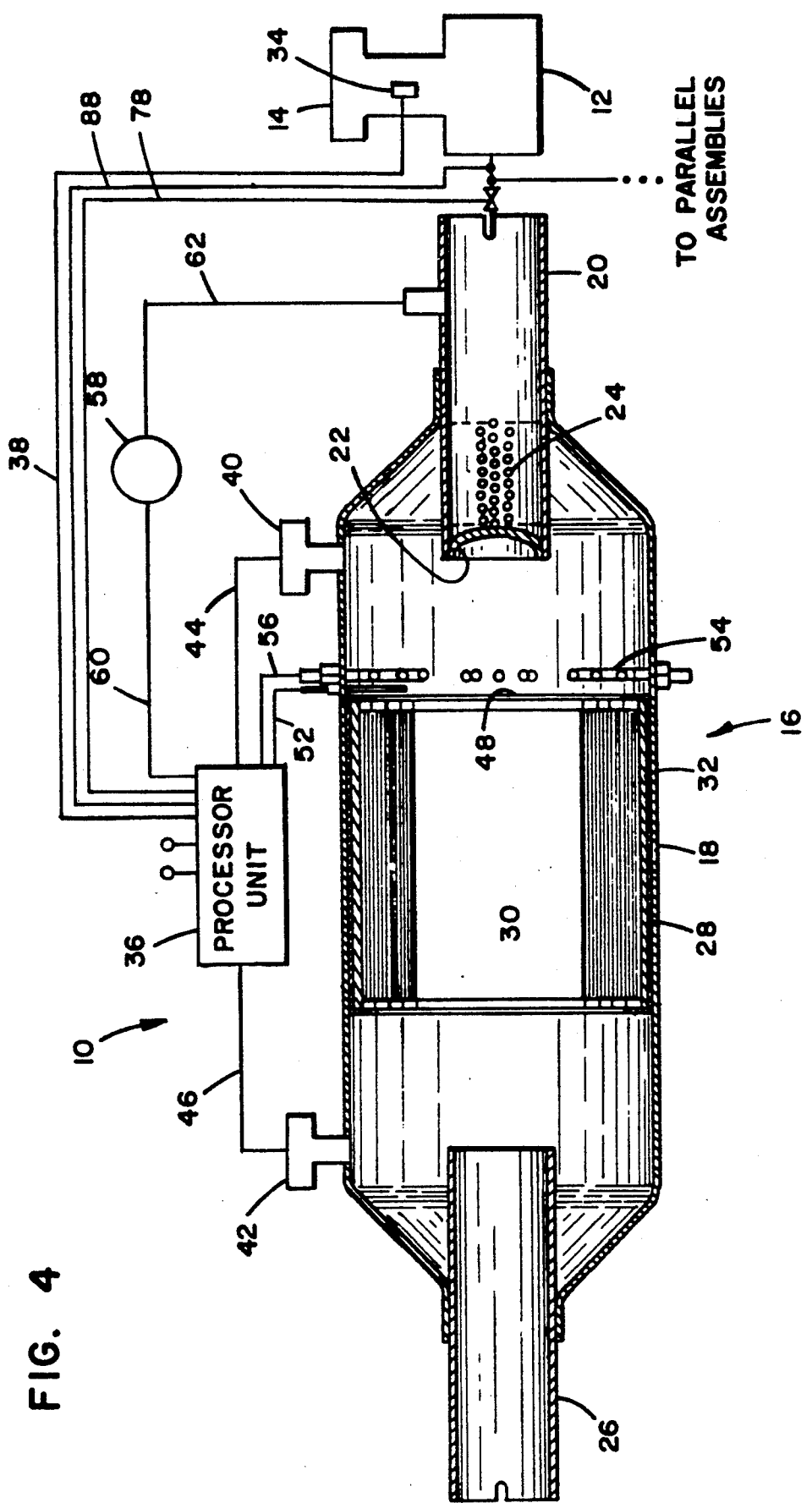
FIG. 4 is a cross-sectional view of filter apparatus together with schematically illustrated regeneration and control apparatus.

In reference to the drawings, wherein like reference numerals throughout the several views designate identical or corresponding parts, and more particularly, with reference to FIG. 1 an engine exhaust treatment system illustrated in accordance with the present invention is designated by the numeral 70. Subsystem 10 is illustrated in FIG. 4 and is representative of a part of system 70. Subsystem 10 is described subsequent to the discussion of system 70 and is described in even greater detail in U.S. patent application Ser. No. 07/399,859, filed Aug. 29, 1989.

System 70 includes an engine 12 having an air intake 14. Exhaust gases from engine 12 are directed through an exhaust line 72 to a plurality of exhaust filtration assemblies 74. Exhaust line 72 is in fluid communication with engine 12 to receive the exhaust gases from engine 12. The exhaust filtration assemblies 74 are connected in parallel with one another with each being in fluid communication with exhaust line 72. In that regard, each assembly 74 includes a valve 76 and a filter device 16. Valve 76 is between engine 12 and filter device 16. Valve 76 is in fluid communication with exhaust line 72 through line 80. Line 82 provides fluid communication from valve 76 to filter device 16. A tailpipe 84 provides an exhaust exit from filter device 16.

System 70 includes a plurality of assemblies 74 wherein the filter devices and valves of the assemblies are identified by $N_i$, $i=1,2,\ldots,n$. The various assemblies, as indicated, are in parallel with one another with all being in fluid communication with exhaust line 72. A representative filter device 16 is described more particularly hereinafter. Appropriate valves for the indicated application are well known to those skilled in the art. Valves 76 are controlled by the processor unit 36 as indicated by line 78.

As described hereinafter, the method in accordance with the present invention of selecting among the multiple filters for placement in the exhaust stream of the engine requires a sensing of air flow to the engine and of backpressure downstream from the engine and upstream from the filters. In particular, air mass flow rate is measured by a sensor 34 near the air intake to engine 12. The measurement is communicated to processor unit 36 via line 38. Sensor 34 is a type known to those skilled in the art, such as a hot wire probe or a venturi style flow meter. Pressure sensor 86 measures backpressure which is communicated to processor unit 36 via line 88. Likewise, pressure sensors of a type suitable to measure backpressure in the indicated environment are well known to those skilled in the art.

Figure 3:
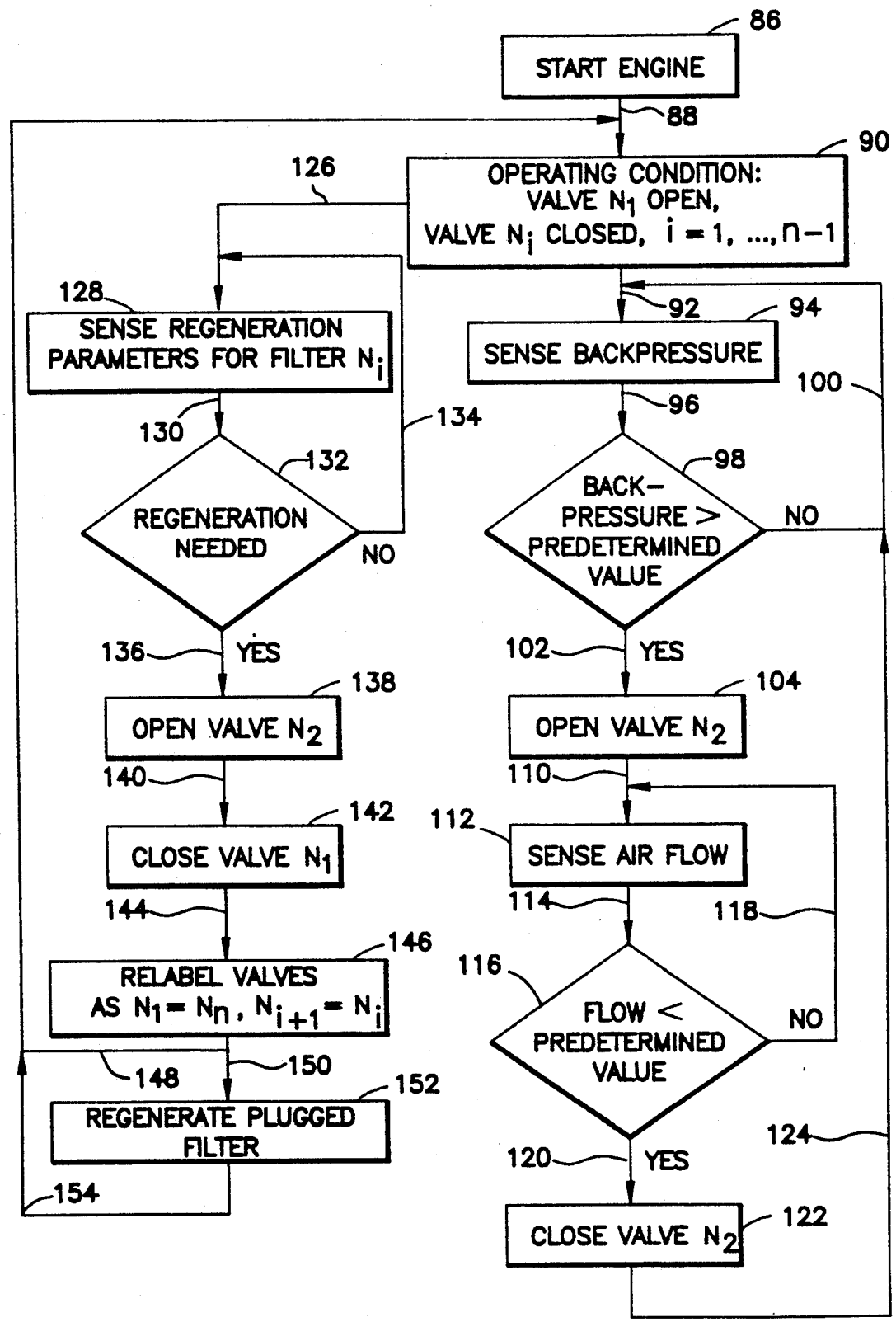
FIG. 3 is a block diagram illustrating the method of use of the system shown in FIG. 1.

The method of use of system 70 is indicated in the flow chart of FIG. 3. When the engine is started as indicated at box 86, line 88 leading to box 90 shows the operating condition to be that valve $N_1$ is open, while the rest of the valves are closed. The various valves and filters of assemblies 74 are identified with a designator N and a subscript i, where $i=1,\ldots,n-1$. As indicated by line 92 leading to box 94, backpressure is sensed and as indicated by line 96 leading to diamond box 98, the sensed backpressure is compared to a predetermined value. If the backpressure is not greater than the predetermined value, then as indicated by line 100, backpressure continues to be sensed. If the backpressure is greater than the predetermined value, then as indicated by line 102 leading to box 104, valve $N_2$ is opened. In a system of, for example, three filters, the opening of valve $N_2$ is acknowledgement that the primary filter has loaded to the point that the exhaust flow from the engine creates a backpressure in trying to flow through the primary filter such that it is greater than an acceptable limit for the engine. Consequently, flow is allowed through the secondary filter, in this case $N_2$. That is, the system has switched from a single filter mode to a double filter mode.

Figure 2:
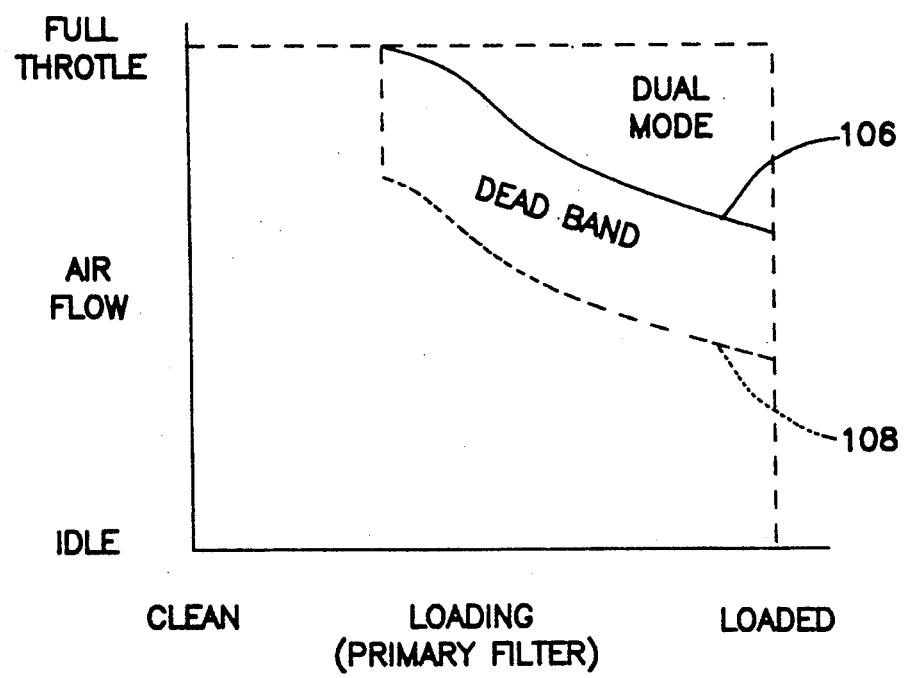
FIG. 2 is an illustrative graph of air flow versus loading of the primary filter.

If the switch from single filter mode to double filter mode occurred as a result of the engine operating at a high throttle so that a high exhaust flow exists, when the engine speed is reduced, it may be appropriate to revert from the double filter mode back to the single filter mode. To prevent excessive switching between modes, it is preferable that the switch back to single filter mode is done at a discrete amount less than the peak air flow for the primary filter at a loading corresponding to the backpressure value which would require placing the secondary filter in the exhaust stream. The discrete amount may be selected for particular engines. Generally, it is preferable that the discrete amount be 70% to 80% of the peak air flow. This concept is illustrated in the graph shown in FIG. 2. A dividing line 106 represents peak air flows allowable through a single filter at various loading levels. A "dead band" region exists and represents the discrete amount less than the peak air flow at which a dual mode configuration continues. When engine air flow falls beneath the lower line 108 of the "dead band", then the secondary filter is removed from the exhaust stream so that the system again returns to a single mode configuration.

The logic just described is indicated in FIG. 3. After valve $N_2$ is opened, as indicated by line 110 leading to box 112, the air flow into the engine is sensed. As indicated by line 114 leading to diamond box 116, the air flow is compared to a predetermined value. The predetermined value is the discrete amount mentioned above to be preferably generally 70% to 80% of the appropriate peak air flow. If the air flow is greater than the predetermined value, then as indicated by line 118, air flow continues to be sensed. If air flow is less than the predetermined value, then as indicated by line 120 leading to box 122, valve $N_2$ is closed. When valve $N_2$ is closed, as indicated by line 124, the sensing of backpressure then again becomes important to determine when it will again be necessary to switch configurations from the single filter mode to the double filter mode.

Appropriate parameters are also sensed to determine when the primary filter must be regenerated. The particular method for determining when regeneration should occur is not part of the present invention. An appropriate method, however, is disclosed hereinafter. It is understood that other parameters and methods may be used in conjunction with system 70 as well.

With further reference to FIG. 3, as indicated by line 126 leading from box 90 which shows the operating condition of the engine to box 128, the regeneration parameters for at least the primary filter $N_1$ should be sensed whenever the engine is operating. As indicated by line 130 leading to diamond box 132, the parameters are sensed so that a decision can be made whether regeneration is needed. If regeneration is not needed, the parameters continue to be sensed as indicated by line 134. If regeneration is needed, as indicated by line 136 leading to box 138, valve $N_2$ is opened. Thereafter, as indicated by line 140 leading to box 142, valve $N_1$ is closed. As indicated by line 144 leading to box 146, the valves (and filters) are then relabelled so that valve $N_1 = N_n$ and $N_i + 1 = N_i$. The indicated relabelling redefines the operating condition of box 90 as indicated by line 148. And, as indicated by line 150 leading to box 152, the plugged filter is regenerated and, as indicated by line 154, is made available for further system operation under the redefinition of designators.

FIGS. 4–8 and the description of them which follows discloses then a particular method for determining whether a filter requires regeneration. The particular method requires the sensing of particular parameters and, as indicated, is exemplary of the type of additional measurements needed and logic required for controlling system 70 in a way which includes bypass regeneration.

With reference to FIG. 1, a subsystem which includes engine 12 and filter device 16 is designated by the numeral 10. Subsystem 10 includes engine 12 having air intake 14. Exhaust gases from engine 12 are directed to filter device 16. Device 16 includes a housing 18 which is substantially cylindrical and has narrowed ends. An inlet pipe 20 is received at one end of housing 18 and is in fluid communication with the exhaust manifold or other such structure of engine 12. Inlet pipe 20 has a closed outlet end 22 and openings 24 to allow exhaust gas to expand from inlet pipe 20 into the entry portion of the chamber formed by housing 18. An outlet pipe 26 is received at the other end of housing 18.

A monolithic ceramic filter is mounted in a can 28 tack welded or otherwise affixed to housing 18. Can 28 has in turned ends to retain filter 30 therein. A heat resistant mat 32 provides insulation and cushioning between a filter element 30 and can 28. A gasket may be used between the filter element and the can at the ends of the mat. A ceramic filter 30 of the type useful with respect to the present invention is commercially available from Industrial Ceramics Department, Ceramics Products Division, Corning Glass Works, Corning, N.Y. 14830. In addition, any fuller discussion of the use of this type of ceramic filter with respect to a regenerative exhaust filtering system may be found in U.S. Pat. No. 4,851,015.

Over time, filter 30 collects an increasing mass of particulates from the exhaust of engine 12, usually in the form of a diesel engine. To maintain filtration effectiveness without creating an excessive backpressure to the engine, filter 30 must be periodically regenerated. A proper combination of differential pressure or pressure drop across filter 30, air mass flow rate into the engine, and air temperature at filter 30 results in a factor which is proportional to captured particle mass. Furthermore, the factor is independent of air flow to the engine, engine speed and exhaust temperature. In any case, the apparatus shown in FIG. 4 depicts sensors to make the indicated measurements so as to control the heating element and, in general, the regeneration of filter 30.

More particularly, air mass flow rate is measured by a sensor 34 near the air intake to engine 12. The sensed measurement is communicated to processor unit 36 via line 38. Pressure sensors 40 and 42 measure pressure upstream and downstream of filter 30 so that a pressure drop can be obtained. Sensors 40 and 42 communicate necessary information to processor unit 36 via lines 44 and 46, respectively, Temperature at the front face 48 of filter 30 is measured by thermocouple 50 which communicates with processor unit 36 via line 52. At the appropriate time as discussed further hereinafter, heating element 54 is turned on via line 56. Combustion air is provided by fan 58 as controlled via line 60 with air directed upstream of filter 30 via line 62.

Figure 6:
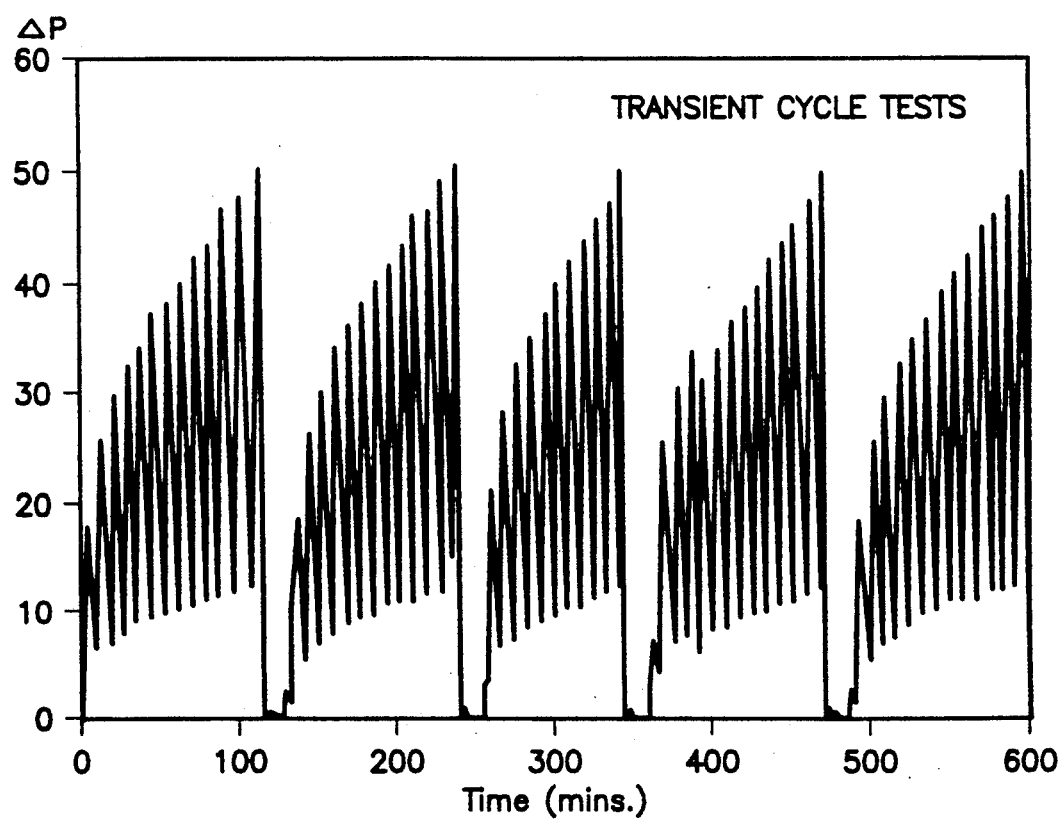
FIG. 6 is a graph of pressure drop across a filter versus time for several cycles of filter loading an for various engine speeds during each cycle.

As indicated previously, known regeneration systems determine when to initiate regeneration by sensing the pressure drop across the ceramic filter or by some other ratio or combination of various pressures and pressure drops. The problem with initiating regeneration based solely on pressure drop is illustrated with reference to FIG. 6. FIG. 6 is a graph of pressure drop across a ceramic filter versus time for several cycles of loading and regeneration. Each of the five cycles extends for approximately 120 minutes. The numerous vertical lines from one regeneration to the next in a particular cycle show the extreme variation in pressure drop across a ceramic filter at transient engine conditions. That is, during any particular cycle the engine was run not only at slow idle, but also at a high speed and various speeds therebetween. If a pressure drop of a value between 10 to 40 inches of water were chosen as a threshold to initiate regeneration, regeneration would have started well before it actually started in the cycles shown. On the other hand, if a threshold of 50 inches of water pressure drop were chosen, the threshold would not have been reached until approximately the time regeneration was done for the cycles shown, but the pressure drop would not have been achieved unless the engine were run at high speed. If circumstances were such that the engine were never run at a high speed, conceivably the ceramic filter could severely overload before the threshold pressure drop were reached resulting in various adverse consequences for the engine and exhaust system. The present invention is directed to removing the variability of initiating regeneration characteristic of prior systems. The present invention, rather, aims to initiate regeneration consistently when a predetermined particle mass has accumulated on the filter.

A factor k can be calculated from pressure drop across the ceramic filter, air mass flow rate (or equivalent) into the engine, and air temperature near the inlet face of the ceramic filter as follows:

$$k = C\left[\frac{\Delta P^x}{Q^y T^z}\right]$$

where C = constant, $\Delta P$ = pressure drop from first obtaining means including sensors 40 and 42, Q = air mass flow rate from said second obtaining means including sensor 34, T = absolute temperature near inlet end of ceramic filter from third obtaining means including thermocouple 50, and where x, y, and z have predetermined values in a range from 0.1 to 2.0.

Figure 7:
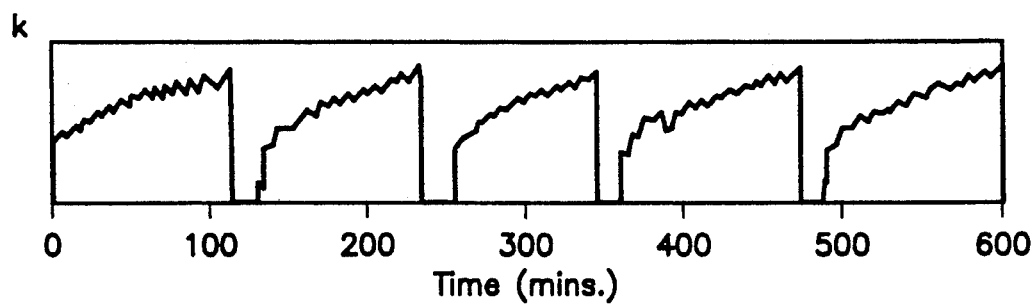
FIG. 7 is a graph of k-factor versus time for the same cycles as FIG. 6.

In appropriate tests, the factor k was found to be proportional to particle mass accumulated on a ceramic filter. The factor k, however, was found to be independent of engine speed and air flow exhaust temperature. With respect to speed, FIG. 7 shows the same engine cycles as FIG. 6. There is no wide variation of values for k in FIG. 7 as there is for pressure drop in FIG. 6 even though engine speed has the exact same variation from slow idle to high speed several times during a particular cycle.

Figure 8:
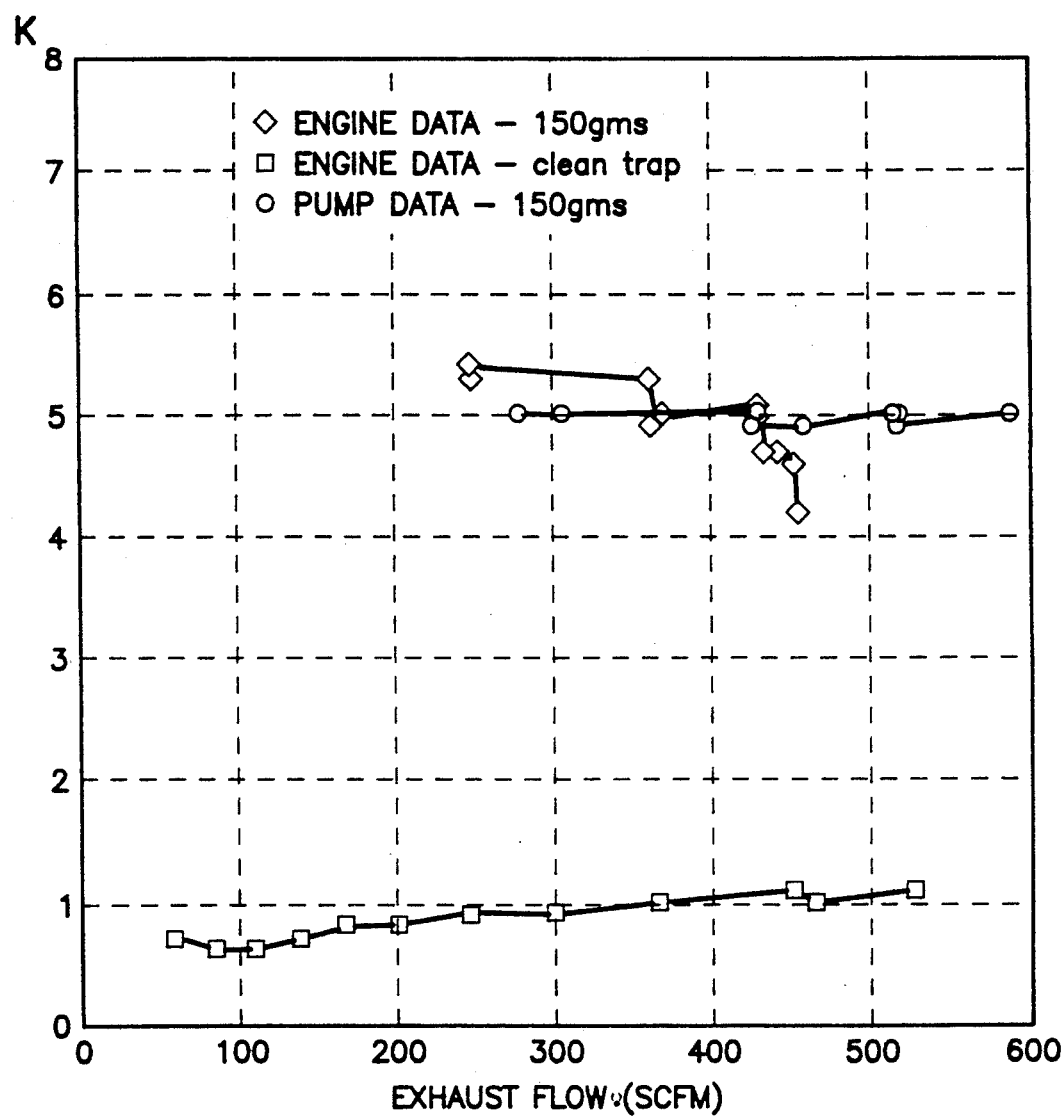
FIG. 8 is a graph of k-factor versus exhaust flow and pump flow for various filter loadings and flow temperatures.

With respect to exhaust flow from the engine, k remains relatively constant as shown in FIG. 8. For a clean trap or filter, k varies from about 0.6 to about 1.1 from a low idle exhaust flow to a high speed engine exhaust flow. There is little more variability for a filter loaded with 150 grams of particulates. That is, k varies from about 5.4 at an exhaust flow of about 460 scfm. Nevertheless, the variation of k for various exhaust flows is substantially less than the variation of pressure drop at various speeds and consequent exhaust flows as illustrated in FIG. 6.

With respect to exhaust temperature, cool air from a pump was blown through a filter loaded with 150 grams of particulates as shown in FIG. 8. The factor k was almost constant at 5.0 and was very similar to the value of k when the heated exhaust gases from the engine were directed through the filter of the same loading. Consequently, exhaust temperature does not appear to have an independent influence on the factor k.

Since the factor k increases monotonically with time and does so without great variation, various values of k relate to various weights of accumulated particulate mass accumulated on the filter. Therefore, a mass value and, consequently, a value of k can be chosen as a threshold for initiating regeneration of the filter. Different values of accumulated mass are appropriate for different sizes of ceramic filter as used with various engines and exhaust systems. An appropriate value is determinable to those skilled in the art.

The values for pressure drop, air mass flow rate, and absolute temperature near the inlet end of the ceramic filter in the equation for calculating k are raised to exponents designated x, y, and z, respectively. The exponents have predetermined values which are determinable by those skilled in the art using a least squares or other equivalent method for matching the curve of an equation to empirical data. In this case, the empirical data is obtained for a particular engine and exhaust system, usually for a particular vehicle. The exponents will have a range depending on the particular system from 0.1 to 2.0. Similarly, the proportionality constant, C, between k and the three measured values is determinable by those skilled in the art in a similar fashion.

Figure 5:
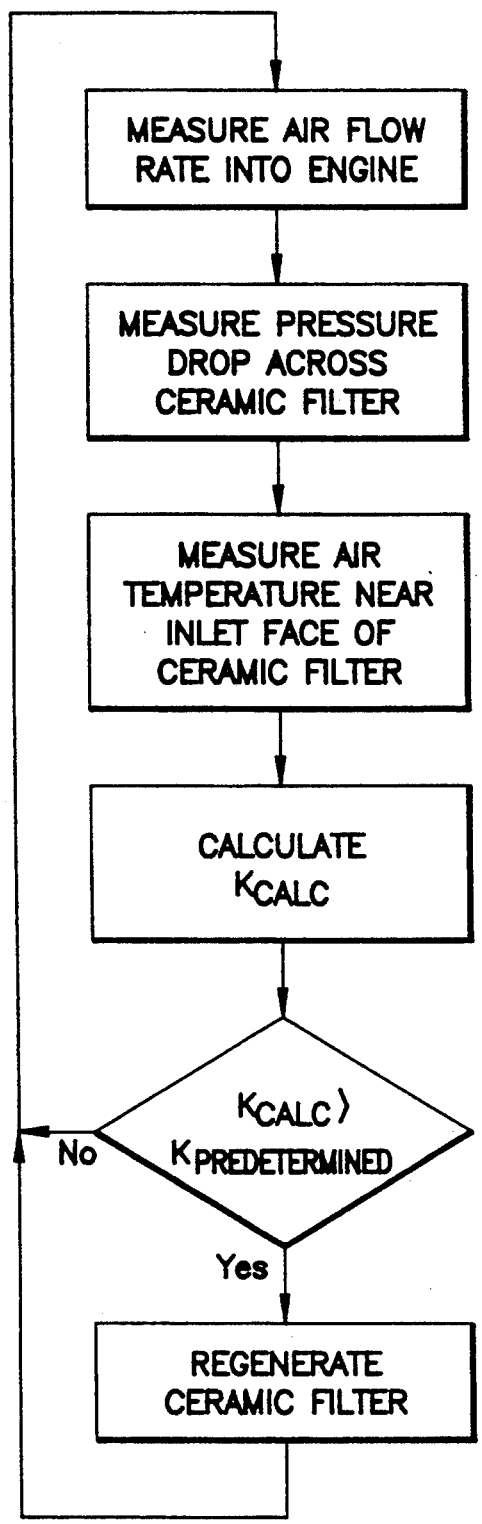
FIG. 5 is a block diagram illustrating the method of use of the apparatus shown in FIG. 4.

In use, as shown in FIG. 5, after the various exponent and proportionality constants have been determined for a particular system, the three various parameters are measured, k is calculated and compared to a predetermined value, and when appropriate, regeneration is initiated. More particularly, air mass flow rate into the engine is obtained based on signal from sensor 34. Pressure drop across the ceramic filter is obtained based on information from pressure transducers 40 and 42. Absolute temperature is obtained based on temperature information measured by thermocouple 50. The data is processed by processor unit 36 to calculate k and compared to a predetermined value of k. When the predetermined threshold value is exceeded, the processing unit provides a mechanism for initiating regeneration. That is, the heating element 54 is turned on and at appropriate times, fan 58 is turned on to provide air. As a part of regeneration, after a flame front is established in filter 30, heating element 54 is turned off. Air from fan 58 must continue to be supplied until combustion is completed. A fuller discussion of a regeneration method appropriate with apparatus disclosed herein is provided in U.S. Pat. No. 4,851,015, hereby incorporated by reference.

Thus, the present invention has been described in detail. It is understood, however, that the disclosure is representative and that equivalents are possible. Consequently, changes made, especially in matters of shape, size, and arrangement of parts or steps are within the principle of the invention to the full extent extended by the meaning of the terms in which the appended claims are expressed.

What is claimed is:

1. A method of selecting among multiple filters for placement in an exhaust stream of an engine for loading with particulates and for removal from said stream for regeneration, comprising the steps of:
   placing a first filter in said stream;
   sensing backpressure in said stream between said filter and said engine;
   placing a second filter in said stream when said backpressure is greater than a first predetermined value;
   sensing air flow to said engine;
   removing said second filter from said stream when said air flow is less than a second predetermined value.

2. The method in accordance with claim 1 wherein said second predetermined value is a discrete amount less than a peak air flow for said first filter at a loading corresponding to a backpressure value which would require placing said second filter in said stream.

3. The method in accordance with claim 2 wherein said discrete amount is 70% to 80%.

4. The method in accordance with claim 1 including sensing parameters for use in a predetermined method of determining when said first filter requires regeneration, and when regeneration is required, placing said second filter in said stream, removing said first filter from said stream, and regenerating said first filter.

5. Apparatus for reducing particulates from exhaust gases of an engine, comprising:
   an exhaust line in fluid communication with said engine to receive the exhaust gases from said engine;
   a plurality of exhaust filtration assemblies connected in parallel with one another with each being in fluid communication with said exhaust line, each of said assemblies including a filter and a valve, said valve being between said engine and said filter;
   means for regenerating said filters;
   means for controlling said regenerating means and said valves to preferentially load a first of said filters and use another of said filters to alleviate backpressure during higher flow conditions until said first is loaded and then preferentially load a second of said filters while alleviating backpressure during higher flow conditions with yet a third of said filters until said second filter is loaded and to continue sequentially loading said filters, said controlling means operating said valves to bypass said filters when loaded and operating said regenerating means to regenerate said filters when loaded and bypassed.

6. The apparatus in accordance with claim 5 wherein said controlling means includes first means for sensing backpressure between said engine and said assemblies, said controlling means further including first means for determining when said backpressure between said preferentially loading filter and said engine is greater than a first predetermined value and including means for operating said valves to alleviate said backpressure with one other of said filters.

7. The apparatus in accordance with claim 6 wherein said controlling means also includes second means for sensing air flow into said engine, said controlling means further including second means for determining when said air flow is less than a second predetermined value, said second predetermined value being a discrete amount less than a peak air flow for said preferentially loading filter at a loading corresponding to a backpressure requiring said one other filter to alleviate said backpressure, said controlling means through said valves operating means causing said exhaust gases to bypass said backpressure alleviating filter when said second determining means determines said air flow is less than said second predetermined value.

8. The apparatus in accordance with claim 7 wherein said discrete amount is 70% to 80%.

9. The apparatus in accordance with claim 5 wherein said controlling means includes third means for determining when said preferentially loaded filter requires regeneration, said apparatus including third means for sensing parameters for use in said third determining means, said controlling means through said valves operating means causing said exhaust gases to bypass said loaded filter when said loaded filter requires regeneration and causing said exhaust gases to be directed through another of said filters, said controlling means operating said regenerating means to regenerate said loaded and bypassed filter.

* * * * *